(12) United States Patent
Straub et al.

(10) Patent No.: US 8,322,236 B2
(45) Date of Patent: Dec. 4, 2012

(54) MEASURING APPARATUS AND METHOD FOR DETECTING MOISTURE AT A MEASUREMENT VOLTAGE INPUT OF THE MEASURING APPARATUS

(75) Inventors: Herman Straub, Rottenburg (DE); Martin Lohmann, Gerlingen (DE); Stephan Buschnakowski, Chemnitz (DE); Jorg Uhle, Limbach-Oberts (DE)

(73) Assignee: Endress + Hauser Conducta Gesellschaft für Mess-und Regeltechnik mbH + Co. KG, Reinach (CH)

( * ) Notice: Subject to any disclaimer, the term of this patent is extended or adjusted under 35 U.S.C. 154(b) by 517 days.

(21) Appl. No.: 12/588,428

(22) Filed: Oct. 15, 2009

(65) Prior Publication Data

US 2010/0109636 A1    May 6, 2010

(30) Foreign Application Priority Data

Oct. 15, 2008    (DE) .................... 10 2008 052 813

(51) Int. Cl.
*G01R 31/02* (2006.01)
*G01R 35/00* (2006.01)
*G01D 3/00* (2006.01)
*G01D 5/16* (2006.01)
*G01N 27/00* (2006.01)

(52) U.S. Cl. ........ 73/866.1; 324/511; 324/603; 340/604
(58) Field of Classification Search ............... 73/1.01, 73/866.1; 324/71.1, 76.11, 511, 602–603, 324/609, 750.3; 340/501, 510, 604–605, 653

See application file for complete search history.

(56) References Cited

U.S. PATENT DOCUMENTS

| | | | | |
|---|---|---|---|---|
| 3,050,662 A | * | 8/1962 | Miller et al. | 361/180 |
| 3,594,637 A | * | 7/1971 | Beckwith | 324/76.77 |
| 4,084,205 A | * | 4/1978 | Bohnert | 361/76 |
| 5,781,024 A | * | 7/1998 | Blomberg et al. | 324/750.02 |
| 5,949,054 A | * | 9/1999 | Karpen et al. | 235/462.25 |
| 6,297,627 B1 | * | 10/2001 | Towne et al. | 324/207.12 |
| 7,358,628 B2 | * | 4/2008 | Yin | 307/134 |
| 2003/0193764 A1 | * | 10/2003 | Ziemer et al. | 361/18 |
| 2004/0130317 A1 | * | 7/2004 | Hatanaka | 324/207.2 |
| 2006/0028069 A1 | * | 2/2006 | Loucks et al. | 307/130 |
| 2006/0247508 A1 | * | 11/2006 | Fennell | 600/345 |
| 2006/0284626 A1 | * | 12/2006 | D'Angelico et al. | 324/708 |
| 2008/0106240 A1 | * | 5/2008 | Sumimoto | 322/15 |

FOREIGN PATENT DOCUMENTS

| | | | | |
|---|---|---|---|---|
| EP | 111815 B | * | 3/1987 | |
| EP | 398509 A2 | * | 11/1990 | |
| EP | 1936390 A1 | * | 6/2008 | |
| JP | 06004932 A | * | 1/1994 | |
| JP | 10019822 A | * | 1/1998 | |
| SU | 1290207 A | * | 2/1987 | |
| WO | WO 9857188 A1 | * | 12/1998 | |

* cited by examiner

*Primary Examiner* — Thomas P Noland
(74) *Attorney, Agent, or Firm* — Bacon & Thomas, PLLC

(57) ABSTRACT

A measuring apparatus having a measurement voltage input with at least one input contact for an input voltage of a measuring element and a method for detecting moisture on the measurement voltage input of such a measuring apparatus are provided, wherein the measuring apparatus includes a supplemental voltage source, which delivers at least one supplemental voltage and is connected with a supplemental contact arranged in the region of the at least one input contact.

19 Claims, 2 Drawing Sheets

MEASURING APPARATUS AND METHOD FOR DETECTING MOISTURE AT A MEASUREMENT VOLTAGE INPUT OF THE MEASURING APPARATUS

TECHNICAL FIELD

The invention relates to a measuring apparatus having a measurement voltage input with at least one input contact for an input voltage UE of a measuring element, and a method for detecting moisture at a measurement voltage input of such a measuring apparatus.

BACKGROUND DISCUSSION

A measuring apparatus of the state of the art for measuring the voltage of a measurement signal of a measuring element, e.g. a sensor element such as, for instance, a glass sensor for measuring the pH-value, is illustrated schematically and simplified in FIG. 1. From the measuring element (not shown), the measurement signal, having an input voltage $U_E$, is conducted through a connection region of a measuring apparatus via the measurement voltage input 1, having at least one input contact 2 and a reference-input contact 7. The connection region in such case must have at least the input contact 2. The reference-input contact 7 is a reference potential, or is connected with a reference potential (e.g. ground). The input contact 2 is connected with a high-resistance input of a voltage follower/impedance converter 8. Following the impedance converter 8, the measurement signal having a measurement voltage $U_M$ can be further processed at low resistance, for example by additional analog signal processing, analog to digital conversion, etc. This will not be described here in greater detail, and is known to those skilled in the art. By means of the high resistance of the impedance converter 8 with its high-ohm input resistance $R_I$, voltage signals of a measuring element with large internal resistance can also be measured, such as, for example, those of glass sensors used for measuring pH-value.

There is, however, in the case of such measuring devices of the state of the art, the disadvantage, that the high-ohm, measurement voltage input 1 is sensitive to electrical disturbances. Thus, for example, leakage resistance paths contacting the high-resistance, measurement voltage input 1 are critical. If an ohmic leakage resistance, schematically represented in FIG. 1 by $R_F$, lies for example, in the range of the size of the internal resistance of the measuring element being used, or if it comes close to the range of the size of this internal resistance of the measuring element, a corruption of the signal of the measuring element occurs. As shown schematically in FIG. 1, the leakage resistance $R_F$ can be considered as a parallel resistance to the input resistance of the measuring apparatus.

A reason for the formation of the leakage resistance $R_F$ at the high-resistance measurement voltage input 1 can be, for example, moisture deposits. In the case of application of an electronic measuring apparatus in the vicinity of liquid media, if a malfunction occurs, a possible cause can be moisture accumulation. This can occur, for instance, in applications in which such an electronic measuring apparatus is applied in liquid analysis as sensor with on-site electronics, i.e. such a measuring apparatus is connected directly and locally with a measuring element, which itself contains liquid media, and/or is operated in liquid media.

If, for example, in the case of such a measuring apparatus, the seal against a liquid medium is defective, for example, through defective mechanical construction or mechanical stress, moisture can get into the electronic measuring apparatus, especially at its measurement voltage input 1. This leads then to a corruption of the measurement results. Thus, in practice, such moisture deposits first form leakage paths with the leakage resistance $R_F$ in the region of the input contact 2 and the reference-input contact 7 of the measurement voltage input 1. Since, as a rule, the connection of the reference-input contact 7 to the reference potential (e.g. ground) is of low resistance, the high-resistance input contact 2 is likewise drawn via the leakage resistance $R_F$ to this reference potential. If the reference potential concerns a possible measurement potential, then based on the measured voltage in such a case, it can no longer be distinguished whether a moisture deposit at the measurement voltage input 1 of the measuring apparatus is present, and thus consequently a corrupting disturbance, or whether the measuring apparatus can be properly operated, wherein from the measuring element, e.g. an input voltage $U_E$ of size in the range of the reference potential is given at the measurement voltage input 1. As a result, a possible leakage resistance $R_F$ thus directly influences the measured variable of a measuring element. Consequently, it is desirable in practice to find an opportunity for safely and reliably determining whether a possible malfunction is present due to emergence of a leakage resistance at a measurement voltage input 1 in a connection region of a measuring apparatus, or whether the measurement is providing an uncorrupted measured value.

SUMMARY OF THE INVENTION

Therefore, an object of the present invention is to provide a measuring apparatus as well as a method for detecting moisture at a measurement voltage input of such a measuring apparatus, which apparatus and method enable detecting moisture in a most simple and reliable manner possible.

This object is achieved by a measuring apparatus having the features of claim 1, as well as by a method for detecting moisture at a measurement voltage input of such a measuring apparatus having the steps of claim 5. Advantageous embodiments and further developments of the invention are the subject matter of each of the dependent claims.

The measuring apparatus of the invention includes: A measurement voltage input having at least one input contact for an input voltage $U_E$ of a measuring element; and a supplemental voltage source, which delivers at least one supplemental voltage $U_Z$ and is connected with a supplemental contact arranged in the region of the at least one input contact.

In accordance with the invention, a supplemental voltage source is thus provided, which, with a supplemental contact, forms a further supplemental grid; without presence of moisture, the supplemental grid is not actually conductively connected with the at least one input contact of the measurement voltage input. However, in accordance with the invention, the supplemental contact is arranged near the region of the at least one (high-resistance) input contact, i.e. at a minimal distance drawn around the high-resistance input contact of a connection region of the measuring apparatus. The supplemental voltage source delivers at least one supplemental voltage $U_Z$ to the supplemental contact. If leakage resistances arise, for example, through moisture occurring in the region of the measurement voltage input of the measuring apparatus of the invention, then a first leakage resistance $R_{F1}$ will occur between the input contact and the supplemental contact of the invention, wherein, through the property of the present supplemental voltage $U_Z$ of the supplemental voltage source, a detection of this occurrence of moisture is possible, since the high-ohm input contact does not drop to the reference potential, as is the case in the state of the art, but, instead, to the potential of the applied supplemental voltage $U_Z$. With knowledge of the properties of this supplemental voltage, a secure identification of this undesired penetration of moisture, and thus the potentially corrupted measurement opportunity, is thereby possible in accordance with the invention. The relatively simple construction of the invention serves for this purpose. Preferably the supplemental voltage $U_Z$ is a fixed voltage. This can be, for example, a positive, or negative, supply voltage.

Thus, in accordance with the invention, with little circuit complexity (only a supplemental voltage source with at least one supplemental voltage $U_Z$ and a supplemental contact, arranged in the region of the at least one input contact, are necessary), a simple registering of the penetration of moisture into the region of the measurement voltage input of a measuring apparatus of the invention can take place. No other change of the subsequent, measured value processing is necessary. The form of the invention is thus also compatible with existing circuits of existing measuring devices. A malfunction of the measurement circuit due to arising moisture can thus be easily detected in accordance with the invention.

Preferably in the case of the measuring apparatus of the invention, the supplemental voltage source can be provided in such a way that it delivers at least one supplemental voltage $U_Z$ of a size, which lies outside of a range of a size of the input voltage $U_E$. Thus, the requirement is preferably only that the supplemental voltage source of the invention delivers a supplemental voltage $U_Z$, which lies outside of the range of the size of the input voltage $U_E$. If penetration of moisture into the region of the contacts of the measurement voltage input takes place, then the high-resistance input contact is not drawn to the potential of the reference input contact, as in the state of the art, but, instead, preferably drawn to outside the range of the values of the input voltage $U_E$ in the direction of the potential of the supplemental voltage $U_Z$ of the supplemental grid. The detection of moisture can thus occur through evaluation of the measurement signal. If the measurement signal leaves the normal measuring range (in the direction of the size of the supplemental voltage $U_Z$), then this is an indication of the penetration of moisture. In contrast, the state of the art so far has been that, in the case of penetration of moisture, the measurement signal, as stated, was drawn to the potential of the reference input contact, thus no departure of the measurement signal from the normal measuring range took place.

In an additional, preferred form of embodiment of the measuring apparatus of the invention, the supplemental voltage source can be provided, such that it delivers at least a first supplemental voltage $U_{Z1}$ and a second supplemental voltage $U_{Z2}$, e.g. with a first supplemental voltage source and a second supplemental voltage source, and such that it has a supplemental voltage switching system, which can switch between the first supplemental voltage $U_{Z1}$ and the second supplemental voltage $U_{Z2}$. Preferably, the second supplemental voltage $U_{Z2}$ in such case can be a positive voltage $V_{CC}$. The first supplemental voltage $U_{Z1}$ can in such case preferably be a reference potential (e.g. ground). The supplemental grid of the invention can, thus, in accordance with this preferred form of embodiment, be alternately switchable between two defined potentials. If moisture now penetrates into the connection region of the measurement voltage input of the measuring apparatus of the invention having this form, this moisture, just as in the case of the previously described form of embodiment of the measuring apparatus of the invention, with high probability first makes contact with the supplemental grid formed of the supplemental contact and supplemental voltage source. In this way, the supplemental grid and the high-resistance input contact are connected via a first leakage resistance $R_{F1}$. In the case of correspondingly high conductivity of the corresponding moisture film, this leads to the input potential being drawn in the direction of the potential of the supplemental voltage $U_Z$ of the supplemental grid. An especially secure detection of the arising moisture can then be enabled with assistance of the supplemental voltage switching system. The voltage curve of the input voltage $U_E$ and/or the measurement voltage $U_M$, as a function of the switching processes in the case of switching from the first supplemental voltage $U_{Z1}$ to the second supplemental voltage $U_{Z2}$ and back, in the presence of a moisture penetration, follows the direction of the voltage change between the two supplemental voltages.

Table 1 shows the corresponding switching steps of the supplemental voltage switching system under the assumption, that $U_{Z1} < U_{Z2}$

| Step | Switching | Moisture really present? | $U_M$ | Moisture detected |
|---|---|---|---|---|
| 1 | $U_{Z1} \rightarrow U_{Z2}$ | Yes | ↑ | Yes |
| 1 | $U_{Z1} \rightarrow U_{Z2}$ | No | — | No |
| 2 | $U_{Z2} \rightarrow U_{Z1}$ | Yes | ↓ | Yes |
| 2 | $U_{Z2} \rightarrow U_{Z1}$ | No | — | No |

Thus only when in accordance with the above Table 1 in step 1 and in step 2, the measurement voltage $U_M$, after the switching, assumes the same direction of change as the voltage change from the first supplemental voltage $U_{Z1}$ to the second supplemental voltage $U_{Z2}$, and correspondingly back, is an electrical connection via the first leakage resistance $R_{F1}$ present, for example due to moisture between the supplemental grid and the high-resistance input contact of the measurement voltage input of the measuring apparatus of the invention.

Also in accordance with this form of embodiment of the measuring apparatus of the invention, a secure and reliable detection of occurring moisture can be achieved in simple manner, wherein here the reliability of detection compared to the first preferred form of embodiment is yet again further increased through the possibility of supplemental voltage switching.

In an additional preferred form of embodiment of the measuring apparatus of the invention, the supplemental voltage source can have a microcontroller for operating the supplemental voltage switching system. Thus, the switching of the supplemental voltage switching system and the recording/evaluating of measured values can be synchronized. The corresponding information is then digitally available in the microcontroller, and can be further processed. In this way the circuit complexity can be still further lessened, and a digital evaluation/processing of the information of the moisture detection of the invention is possible.

In the context of the present invention, a method is also provided, according to claim 5, for detecting moisture at a measurement voltage input of a measuring apparatus having at least one input contact for an input voltage $U_E$ of a measuring element, wherein, in the case of this method, in accordance with the invention, a supplemental voltage source and a supplemental contact connected with the supplemental voltage source, which contact is arranged in the region of the at least one input contact, are used, wherein at least one supplemental voltage $U_Z$ is generated from the supplemental voltage source and applied to the supplemental contact, such that, in the case of occurrence of moisture in the region of the at least one input contact, a parallel circuit is produced between the at least one input contact and the supplemental contact, so that a size of the input voltage $U_E$, or, as a result, also the measurement voltage $U_M$, is drawn in the direction of a size of the at least one supplemental voltage $U_Z$. The corresponding steps during the course of the method of the invention have already been described above in connection with the presentation of the measuring apparatus of the invention.

Preferably in the method of the invention, the supplemental voltage $U_Z$ can be supplied with a size which lies outside of a range of a size of the input voltage $U_E$.

Additionally in the case of the method of the invention, preferably through switching between at least a first supplemental voltage $U_{Z1}$ and a second supplemental voltage $U_{Z2}$, a still further improved detection of moisture can be achieved. Preferably, in such case, as second supplemental voltage $U_{Z2}$, a positive voltage $V_{CC}$ can be applied.

Furthermore, with regard to the method of the invention, the corresponding embodiments in connection with the apparatus of the invention should be referenced, wherein the apparatus of the invention is correspondingly provided and designed for executing the method of the invention.

On the whole, the present invention enables, in simple and reliable manner, moisture detection at a measurement voltage input of a measuring apparatus.

BRIEF DESCRIPTION OF THE DRAWINGS

The invention will now be explained in greater detail on the basis of three examples of embodiments illustrated in the appended drawings, the figures of which show as follows.

DETAILED DISCUSSION IN CONJUNCTION WITH THE DRAWINGS

Figure 1:
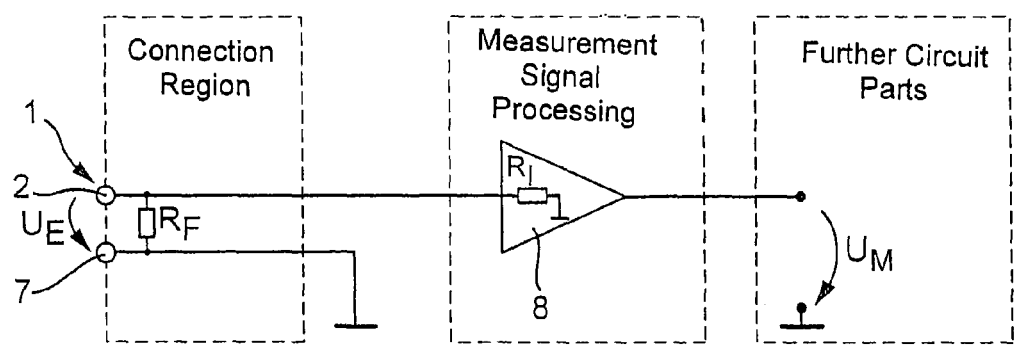
FIG. 1 is a schematic view of a measuring apparatus according to the state of the art.

FIG. 1 shows a schematic view of a measuring apparatus according to the state of the art, as such has already been described above.

Figure 2:
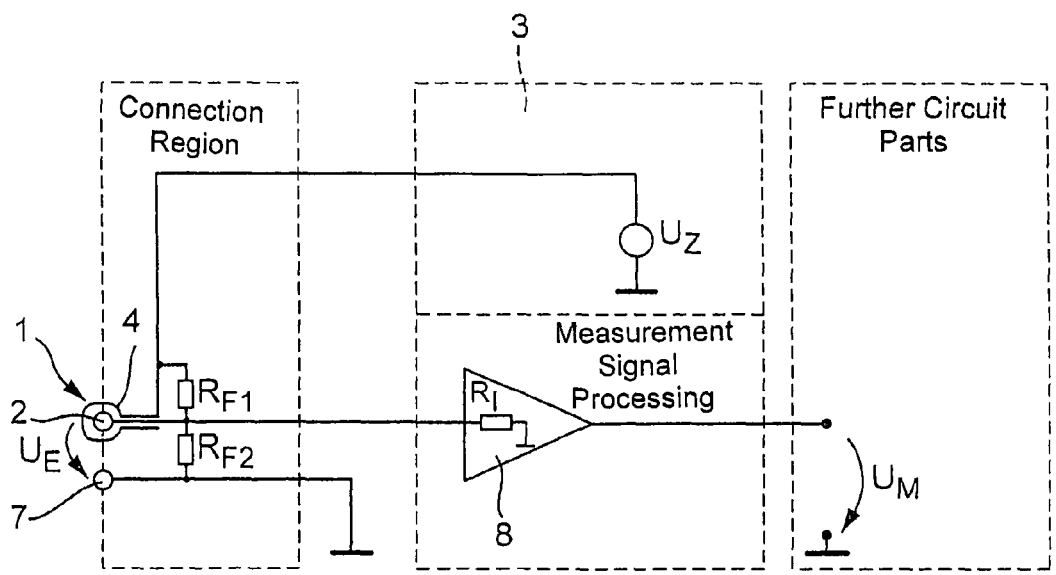
FIG. 2 is a schematic view of a first example of an embodiment of a measuring apparatus of the invention.

FIG. 2 shows a schematic illustration of a first example of an embodiment of a measuring apparatus of the invention. In a connection region of the measuring apparatus of the invention, a measurement voltage input 1 is provided, to which an input voltage $U_E$ of a measuring element (not shown in this figure and the remaining figures) is supplied. The measurement voltage input 1 includes at least one input contact 2. Additionally, a reference-input contact 7 is provided, which is grounded to provide a reference potential. In the region of the input contact 2, in accordance with the invention, a supplemental contact 4 is provided, which surrounds the input contact 2 as far as possible. This supplemental contact 4 is connected with a supplemental voltage source 3, which delivers a supplemental voltage $U_Z$, and thus forms a supplemental grid. A unit for measurement signal processing includes an impedance converter 8 with an internal resistance $R_I$, wherein the input of the impedance converter is connected with the (high-resistance) input contact 2 of the measurement voltage input 1. In further circuit parts, the measurement signal emitted by the impedance converter 8 can be additionally processed with a measurement voltage $U_M$ in known manner.

In case of an occurrence of moisture in the region of the connection region of the measurement voltage input 1, a first leakage resistance $R_{F1}$ arises between the input contact 2 and the supplemental contact 4 and a second leakage resistance $R_{F2}$ between the input contact 2 and the reference-input contact 7. According to the invention, via the first leakage resistance $R_{F2}$, the potential of the input contact 2 is drawn in the direction of the potential of the supplemental voltage $U_Z$ of the supplemental voltage source 3. If, now, the size of the potential of the supplemental voltage $U_Z$ lies outside the range of the input voltage $U_E$, the presence of moisture in the connection region can, according to the invention, be detected simply due to the departure of the input voltage $U_E$ from the normal range of the measurement voltage input, input voltage $U_E$, or due to the corresponding departure of the measurement voltage $U_M$ from the normal range of the measurement voltage $U_M$.

Figure 3:
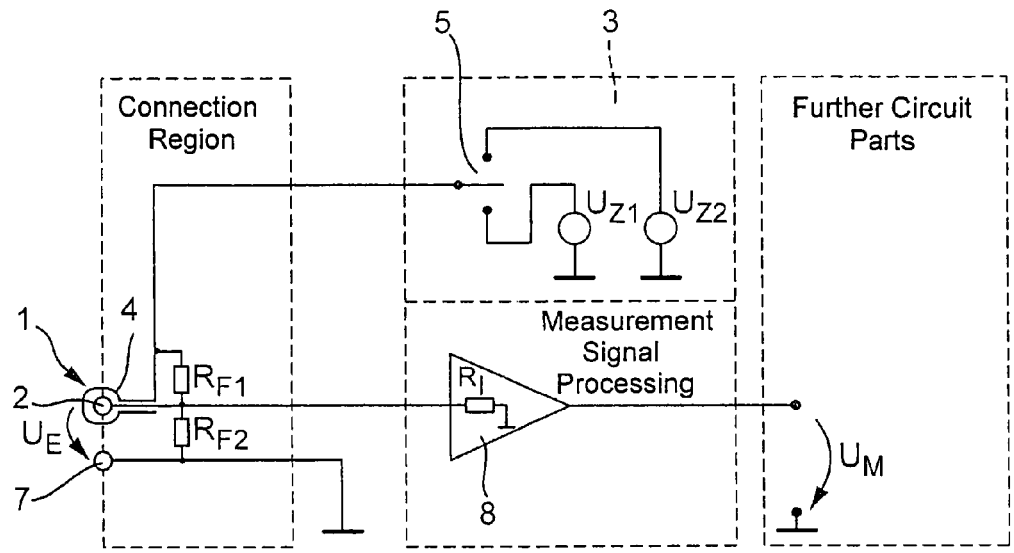
FIG. 3 is a schematic view of a second example of an embodiment of a measuring apparatus of the invention.

FIG. 3 shows schematically a second example of an embodiment of a measuring apparatus of the invention. Likewise as in the case of the preceding example of an embodiment in FIG. 2, here, the occurrence of moisture in the region of the connection region of the measuring apparatus of the invention is represented by the corresponding leakage resistances, namely the first leakage resistance $R_{F1}$ and the second leakage resistance $R_{F2}$. Here, detection of a corrupted measurement of moisture occurs by embodying the supplemental voltage source 3 of the invention to include a supplemental voltage switching system 5, which is switchable between a first supplemental voltage $U_{Z1}$ and a second supplemental voltage $U_{Z2}$ of the supplemental voltage source 3. The remaining elements of FIG. 3 correspond to the elements already illustrated in FIG. 2.

In the form of embodiment of the measuring apparatus of the invention illustrated in FIG. 3, thus, the supplemental grid, formed from a supplemental voltage source 3 having a first supplemental voltage source for a first supplemental voltage $U_{Z1}$ and a second supplemental voltage source for a second supplemental voltage $U_{Z2}$, the supplemental voltage switching system 5 and the supplemental contact 4, can be switched alternately between two defined potentials. If, now, moisture penetrates into the connection region of the measurement voltage input of the measuring apparatus of the invention with this embodiment, the supplemental grid and the high-ohm input contact 2 become connected via the first leakage resistance $R_{F1}$ and the input potential is drawn in the direction of the potential of the supplemental voltage $U_Z$ of the supplemental grid, wherein due to the switchability of the supplemental voltage $U_Z$ between a first supplemental voltage $U_{Z1}$ and a second supplemental voltage $U_{Z2}$, the voltage curve of the input voltage $U_E$ and/or the measurement voltage $U_M$ will, as a function of the switching events in the case of switching from the first supplemental voltage $U_{Z1}$ to the second supplemental voltage $U_{Z2}$ and back, follow the direction of the voltage change between the two supplemental voltages.

Figure 4:
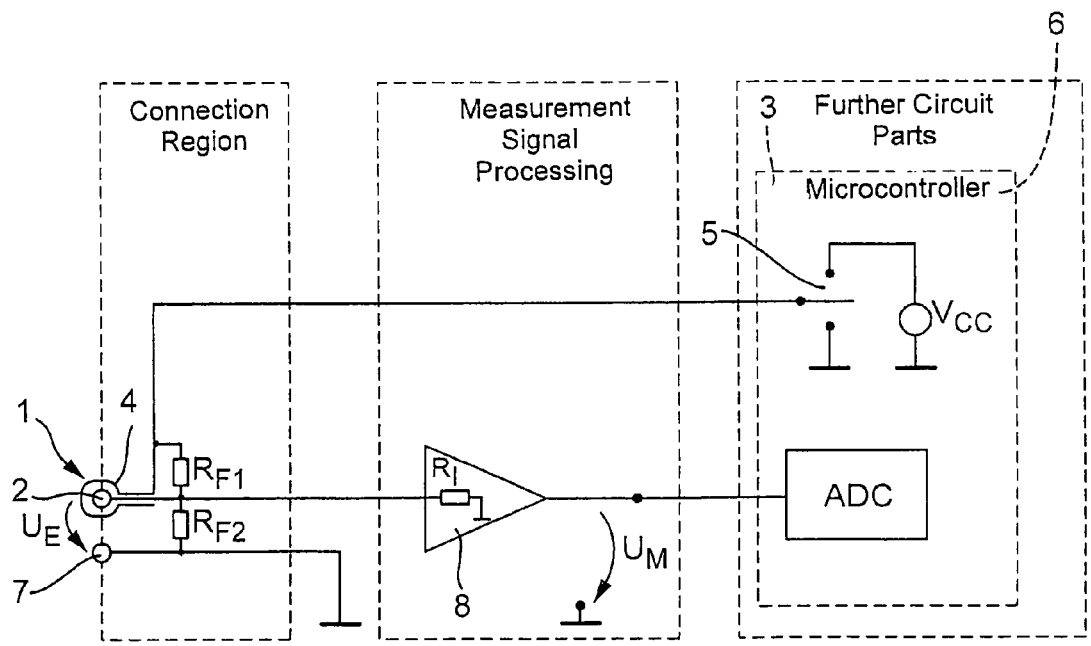
FIG. 4 is a schematic view of a third example of an embodiment of a measuring apparatus of the invention.

FIG. 4 shows, schematically, a third example of an embodiment of a measuring apparatus of the invention, which corresponds essentially to the second example of an embodiment in FIG. 3. Likewise as in the case of the preceding, second example of an embodiment the FIG. 3, in this measuring apparatus, a supplemental voltage switching system 5 is also provided. This switches, according to the invention, between a ground, reference potential (corresponds to e.g. the first supplemental voltage $U_{Z1}$ in the second example of an embodiment) and a preferably positive voltage $V_{CC}$ (corresponds to e.g. the second supplemental voltage $U_2$ in the second example of an embodiment), wherein the control in such case occurs via a microcontroller 6. The signal processing occurs via an analog to digital converter (ADC).

As regards a possible circuit board layout, it is to noted, that the supplemental grid, especially in a region, in which moisture accumulation is to be reckoned with, thus e.g. in the connection region, should not be covered with solder resist, since then no contact especially of the supplemental contact with moisture could occur.

The invention claimed is:

1. A measuring apparatus comprising:
   a measurement voltage input comprising at least one input contact for an input voltage of a measuring element;
   an impedance converter, wherein a high-resistance input of said impedance converter is connected to said at least one input contact of said measurement voltage input, said impedance converter emitting a measurement signal;
   a supplemental contact; and
   a supplemental voltage source, which delivers at least one supplemental voltage and which is connected with said supplemental contact forming a supplemental grid, said supplemental grid being not conductively connected with the at least one input contact of the measurement voltage input, without presence of moisture, wherein:
   said supplemental contact is arranged in the region of said at least one input contact.

2. The measuring apparatus as claimed in claim 1, wherein:
   said supplemental voltage source is so provided, that it delivers at least one supplemental voltage of a size, which lies outside of a range of a size of the input voltage.

3. The measuring apparatus as claimed in claim 1, wherein:
   said supplemental voltage source is so provided, that it delivers at least a first supplemental voltage and a second supplemental voltage and includes a supplemental voltage switching system, which can be switched between the first supplemental voltage and the second supplemental voltage; and
   the second supplemental voltage is a positive voltage.

4. The measuring apparatus as claimed in claim 3, wherein:
   said supplemental voltage source includes a microcontroller for operating said supplemental voltage switching system.

5. The measuring apparatus as claimed in claim 1, wherein:
   said measurement voltage input further comprising a reference input contact, which is grounded to provide a reference potential.

6. A method for detecting moisture on a measurement voltage input of a measuring apparatus comprising at least one input contact for an input voltage of a measuring element, comprising the steps of:
   applying an input voltage of said measuring instrument to said at least one input contact, which is connected to a high-resistance input of an impedance converter, said impedance converter emitting a measurement signal;
   producing at least one supplemental voltage by use of a supplemental voltage source and a supplemental contact connected with the supplemental voltage source and arranged in the region of the at least one input contact; and
   said supplemental voltage being applied to the supplemental contact, so that, in the case of occurrence of moisture in the region of the at least one input contact, a shunt connection is produced between the at least one input contact and the supplemental contact, so that a size of the input voltage is drawn in the direction of a size of the at least one supplemental voltage.

7. The method as claimed in claim 6, wherein:
   a supplemental voltage with a size is delivered, which lies outside of a range of a size of the input voltage.

8. The method as claimed in claim 7, further comprising:
   detecting the presence of moisture in the region of the at least one input contact due to the departure of the input voltage from a normal range of the measurement voltage input or due to the departure of the measurement voltage from a normal range of the measurement voltage.

9. The method as claimed in claim 6, further comprising the step of:
   switching between at least a first supplemental voltage and a second supplemental voltage.

10. The method as claimed in claim 9, further comprising:
    detecting the presence of moisture in the region of the at least one input contact, when the measurement voltage after the switching assumes the same direction of change as the voltage change from the first supplemental voltage to the second supplemental voltage.

11. The method as claimed in claim 6, wherein:
    said measuring element being a glass sensor for measuring pH-value.

12. A measuring apparatus, comprising:
    a measuring element with large internal resistance, a measurement voltage input comprising at least one input contact for an input voltage of said measuring element connected to said voltage input;
    a unit for measurement signal processing comprising an impedance converter, wherein a high-resistance input of said impedance converter is connected to said at least one input contact of said measurement voltage input, said impedance converter providing a measurement signal;
    a supplemental contact, which is arranged in the region of said at least one input contact; and
    a supplemental voltage source, which delivers at least one supplemental voltage and is connected with said supplemental contact.

13. The measuring apparatus as claimed in claim 12, wherein:
    said measuring element with large internal resistance being a glass sensor for measuring pH-value.

14. The measuring apparatus as claimed in claim 12, further comprising:
    further circuit parts for additional processing said measurement signal.

15. The measuring apparatus as claimed in claim 12, wherein:
    said supplemental contact surrounds said input contact.

16. The measuring apparatus as claimed in claim 12, wherein:
    said measurement voltage input further comprising a reference input contact, which is grounded to provide a reference potential.

17. The measuring apparatus as claimed in claim 12, wherein:
    said supplemental voltage source is so provided, that it delivers at least one supplemental voltage of a size, which lies outside of a range of a size of the input voltage.

18. The measuring apparatus as claimed in claim 12, wherein:
    said supplemental voltage source is so provided, that it delivers at least a first supplemental voltage and a second supplemental voltage and includes a supplemental voltage switching system, which can be switched between the first supplemental voltage and the second supplemental voltage; and said second supplemental voltage is preferably a positive voltage.

19. The measuring apparatus as claimed in claim 12, wherein:

said supplemental voltage source and said supplemental contact are connected forming a supplemental grid, said supplemental grid being not conductively connected with the at least one input contact of the measurement voltage input, without presence of moisture.

* * * * *